(12) United States Patent
Kato et al.

(10) Patent No.: US 12,065,152 B2
(45) Date of Patent: Aug. 20, 2024

(54) DRIVE ASSIST SYSTEM

(71) Applicant: SUBARU CORPORATION, Tokyo (JP)

(72) Inventors: Toru Kato, Tokyo (JP); Ryota Nakamura, Tokyo (JP); Tsukasa Mikuni, Tokyo (JP); Masatoshi Tsuge, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 222 days.

(21) Appl. No.: 17/698,342

(22) Filed: Mar. 18, 2022

(65) Prior Publication Data
US 2022/0315017 A1 Oct. 6, 2022

(30) Foreign Application Priority Data
Mar. 30, 2021 (JP) ................................ 2021-058856

(51) Int. Cl.
*B60W 50/00* (2006.01)
*A61B 5/00* (2006.01)
(Continued)

(52) U.S. Cl.
CPC .......... *B60W 50/0098* (2013.01); *A61B 5/18* (2013.01); *A61B 5/4815* (2013.01); *A61B 5/6893* (2013.01); *B60W 40/08* (2013.01); *B60W 2040/0827* (2013.01); *B60W 2520/04* (2013.01); *B60W 2540/106* (2013.01); *B60W 2540/16* (2013.01); *B60W 2540/18* (2013.01); *B60W 2540/229* (2020.02); *B60W 2710/1005* (2013.01); *B60W 2710/205* (2013.01); *B60W 2720/106* (2013.01)

(58) Field of Classification Search
CPC .................... B60W 50/0098; B60W 2540/229
See application file for complete search history.

(56) References Cited

U.S. PATENT DOCUMENTS

2014/0210625 A1* 7/2014 Nemat-Nasser ....... G08B 21/06 340/575
2017/0053513 A1* 2/2017 Savolainen ............... B60L 3/02
(Continued)

FOREIGN PATENT DOCUMENTS

JP 2020-082906 A 6/2020

*Primary Examiner* — Long T Tran
(74) *Attorney, Agent, or Firm* — Rimon P.C.

(57) ABSTRACT

A drive assist system includes an occupant monitoring apparatus, a determination apparatus, and a drive assist control apparatus. The occupant monitoring apparatus monitors a physical state of an occupant, including a driver, of a vehicle. The determination apparatus determines a traveling state and a stopped state of the vehicle. The drive assist control apparatus executes a control to secure safe traveling upon determining that sleep duration of the occupant is less than a predetermined time and quality of sleep thereof is lower than a predetermined level on the basis of monitoring information acquired by the occupant monitoring apparatus. The drive assist control apparatus includes one or more processors that perform, in a case where determination information from the determination apparatus indicates the stopped state, a control of appropriately restricting the driver's driving operation on the basis of at least the sleep duration and the quality of sleep of the driver.

18 Claims, 14 Drawing Sheets

(51) Int. Cl.
*A61B 5/18* (2006.01)
*B60W 40/08* (2012.01)

(56) References Cited

U.S. PATENT DOCUMENTS

| | | | |
|---|---|---|---|
| 2017/0143253 A1* | 5/2017 | Krenzer | A61B 5/4809 |
| 2020/0283028 A1* | 9/2020 | Oba | B60W 50/14 |
| 2020/0302187 A1* | 9/2020 | Wang | H04L 25/0204 |
| 2020/0383580 A1* | 12/2020 | Shouldice | A61B 5/02416 |
| 2021/0188289 A1* | 6/2021 | Oba | G06V 20/597 |

* cited by examiner

| DATE | ACCUMULATED SLEEP DURATION |
|---|---|
| 2021/3/A | 0h43m |
| 2021/3/B | 1h55m |
| 2021/3/C | 1h51m |
| 2021/3/D | 0h32m |
| 2021/3/E | 2h06m |
| 2021/3/F | 2h12m |
| 2021/3/G | 1h48m |

FIG. 3

| DATE | ACCUMULATED SLEEP DURATION |
|---|---|
| 2021/2/A | 7h11m |
| 2021/2/B | 6h45m |
| 2021/2/C | 6h51m |
| 2021/2/D | 3h32m |
| 2021/2/E | 7h06m |
| 2021/2/F | 7h22m |
| 2021/2/G | 6h48m |

FIG. 7

DRIVE ASSIST SYSTEM

CROSS-REFERENCE TO RELATED APPLICATIONS

The present application claims priority from Japanese Patent Application No. 2021-058856 filed on Mar. 30, 2021, the entire contents of which are hereby incorporated by reference.

BACKGROUND

The technology relates to a drive assist system.

In general, at a driving start timing of a vehicle, it is difficult to determine a sleep state of an occupant, including a driver, inside the vehicle and to also determine the degree of the sleep state of the occupant.

Meanwhile, the following technique is disclosed regarding sleepiness of a driver. That is, a sleepiness level of the driver is detected, and whether awakening assistance for the driver is necessary is determined on the basis of the detected sleepiness level. In a case where the awakening assistance is necessary, a driver's seat is vibrated at least in some time slots with use of a vibration wave in which a first frequency promoting muscle tone and a second frequency suppressing muscle tone are imposed on each other. Such a technique is disclosed, for example, in Japanese Unexamined Patent Application Publication (JP-A) No. 2020-082906.

SUMMARY

An aspect of the technology provides a drive assist system, to be applied to a vehicle, that includes an occupant monitoring apparatus, a determination apparatus, and a drive assist control apparatus. The occupant monitoring apparatus is configured to monitor a physical state of an occupant of the vehicle. The occupant includes a driver of the vehicle. The determination apparatus is configured to determine a traveling state and a stopped state of the vehicle. The drive assist control apparatus is configured to execute a control adapted to secure safe traveling of the vehicle in a case where the drive assist control apparatus determines that sleep duration of the occupant is less than a predetermined time and quality of sleep of the occupant is lower than a predetermined level on the basis of monitoring information acquired by the occupant monitoring apparatus. The drive assist control apparatus includes one or more processors and one or more memories. The one or more memories are coupled to the one or more processors to communicate with the one or more processors. The one or more processors are configured to perform, in a case where determination information from the determination apparatus indicates that the vehicle is in the stopped state, a control of appropriately restricting a driving operation, performed by the driver, on the basis of at least the sleep duration and the quality of sleep of the driver.

BRIEF DESCRIPTION OF THE DRAWINGS

The accompanying drawings are included to provide a further understanding of the disclosure, and are incorporated in and constitute a part of this specification. The drawings illustrate embodiments and, together with the specification, serve to explain the principles of the disclosure.

FIG. 3 is a diagram illustrating an example of a concept used in a case where the drive control apparatus of the drive assist system according to the example embodiment of the technology sets a predetermined time.

FIG. 7 is a diagram illustrating an example of a concept used in a case where the drive control apparatus of the drive assist system according to the example embodiment of the technology sets a predetermined time.

DETAILED DESCRIPTION

Figure 1:
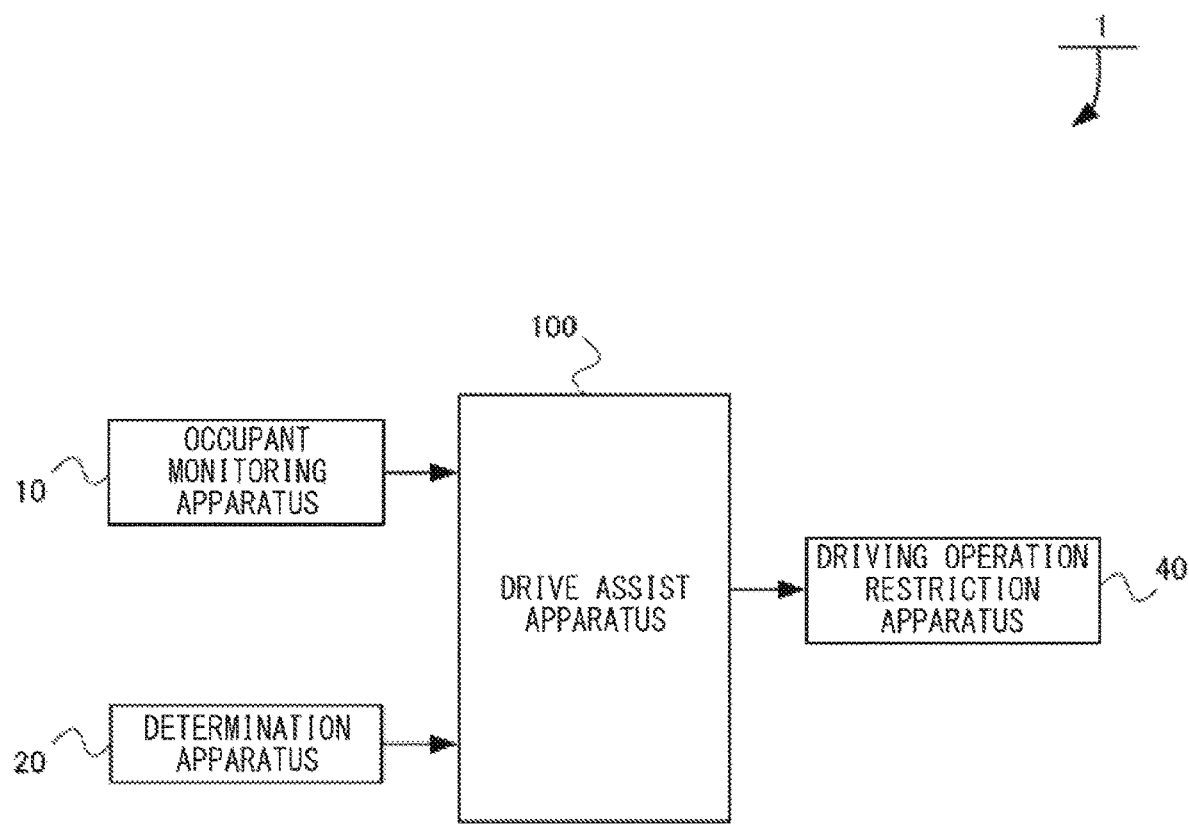
FIG. 1 is a diagram illustrating an example of a configuration of a drive assist system according to an example embodiment of the technology.

A technique disclosed in JP-A No. 2020-082906 is merely for determining a sleepiness level of a driver of a vehicle in the middle of traveling of the vehicle. Therefore, it is difficult to determine a sleep state of an occupant, including the driver, inside the vehicle and perform drive assistance for safe traveling of the vehicle at a driving start timing of the vehicle.

It is desirable to provide a drive assist system that determines a sleep state of an occupant, including a driver, inside a vehicle and performs appropriate drive assistance for safe traveling of the vehicle at a driving start timing of the vehicle.

In the following, some example embodiments of the technology are described with reference to FIGS. 1 to 14. Note that the following description is directed to illustrative examples of the disclosure and not to be construed as limiting to the technology. In each of the drawings referred to in the following description, elements have different scales in order to illustrate the respective elements with sizes recognizable in the drawings. Therefore, factors including, without limitation, the number of each of the elements, the shape of each of the elements, a size of each of the elements, a ratio between the elements, and relative positional relationship between the elements are illustrative only and not to be construed as limiting to the technology. Further, elements in the following example embodiments which are not recited in a most-generic independent claim of the disclosure are optional and may be provided on an as-needed basis. Throughout the present specification and the drawings, elements having substantially the same function and configuration are denoted with the same numerals to avoid any redundant description.

First Example Embodiment

Referring to FIGS. 1 to 4, a drive assist system 1 according to a first example embodiment of the technology is described.

[Configuration of Drive Assist System 1]

As illustrated in FIG. 1, the drive assist system 1 according to the first example embodiment may include an occupant monitoring apparatus 10, a determination apparatus 20, a driving operation restriction apparatus 40, and a drive assist apparatus 100. The occupant monitoring apparatus 10 monitors a physical state of an occupant of a vehicle. As used herein, the term "occupant" encompasses a driver. Non-limiting examples of the physical state of the occupant of the vehicle may include a behavior, a facial expression, and a health condition of the occupant of the vehicle.

The occupant monitoring apparatus 10 may use, for example, a camera to monitor the physical state or the like of the occupant of the vehicle. The camera may include, for example, a built-in imaging device such as a charge coupled device (CCD) or a complementary metal oxide semiconductor (CMOS) image sensor (CIS), and acquire an image, including a moving image and a still image, of the occupant of the vehicle captured by the imaging device.

In one example embodiment, the camera may include both an optical camera and a near-infrared ray camera.

Non-limiting examples of information to be acquired from the occupant monitoring apparatus 10 may include an opening degree of an eye, the number of times of blinking, sleep duration, rest duration, and the number of times of rolling while sleeping.

The determination apparatus 20 determines a traveling state and a stopped state of the vehicle. The determination apparatus 20 may include, for example but not limited to, an ignition switch that determines a state of an ignition key. For example, in a case where the ignition key is at an ON position, the determination apparatus 20 may determine that the vehicle is in the traveling state. In a case where the ignition key is at an OFF position, the determination apparatus 20 may determine that the vehicle is in the stopped state.

Note that, the term "traveling state" encompasses not only a state in which the vehicle is actually traveling but also a state in which the vehicle is ready to travel.

The driving operation restriction apparatus 40 appropriately restricts a driving operation, performed by the driver, on the basis of at least the sleep duration and quality of sleep of the driver among the occupants of the vehicle in a case where determination information from the determination apparatus 20 indicates that the vehicle is in the stopped state.

Non-limiting examples of the driving operation restriction apparatus 40 may include a power steering apparatus, an acceleration limiter apparatus, and a shift apparatus.

The drive assist apparatus 100 may execute a control adapted to secure safe traveling of the vehicle, in a case where the drive assist apparatus 100 determines that the sleep duration at least of the driver among the occupants is less than a predetermined time and that the quality of sleep at least of the driver among the occupants is lower than a predetermined level on the basis of monitoring information acquired by the occupant monitoring apparatus 10.

A configuration of the drive assist apparatus 100 and a process to be performed by the drive assist apparatus 100 may be described in detail later.

[Configuration of Drive Assist Apparatus 100]

Figure 2:
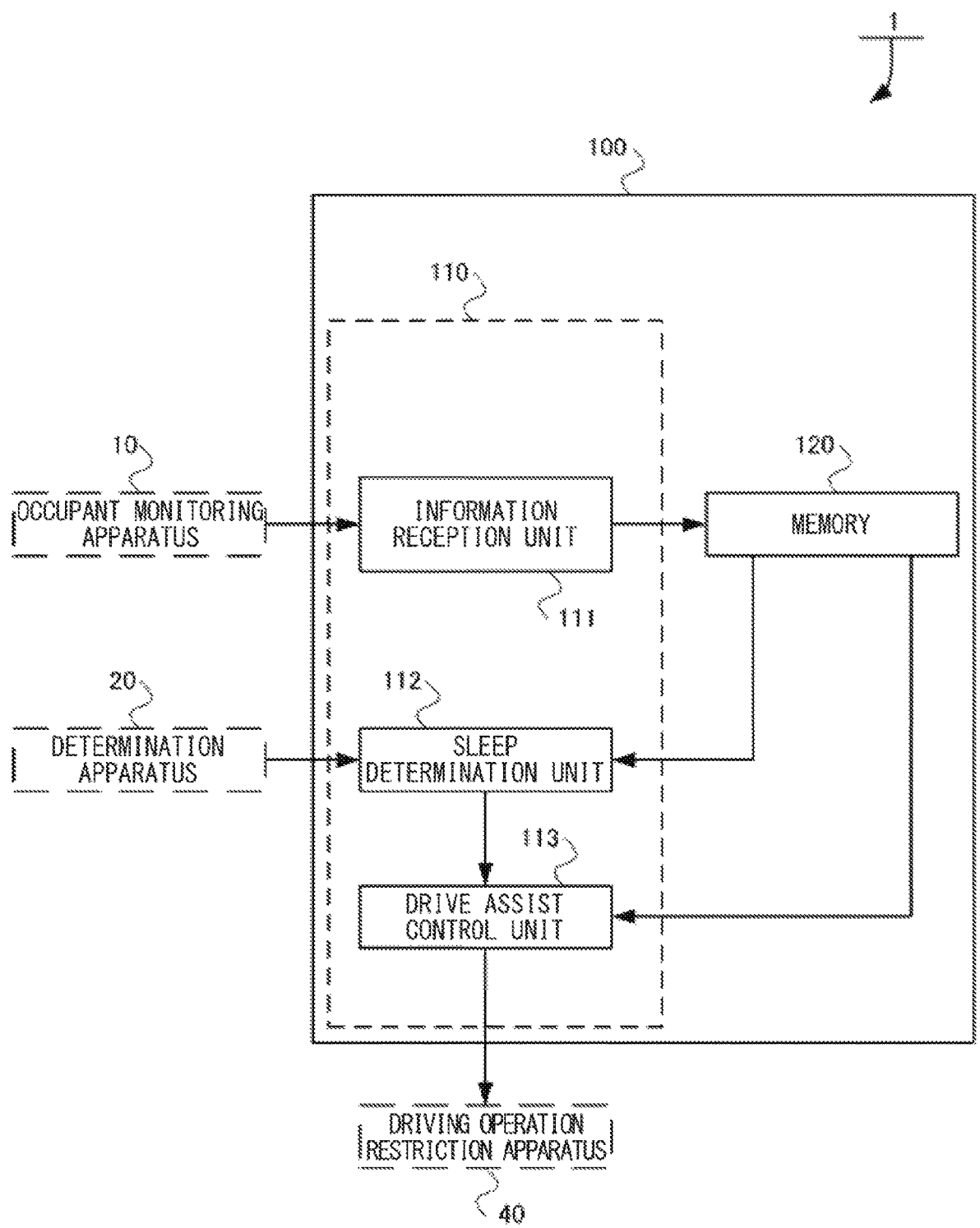
FIG. 2 is a diagram illustrating an example of a configuration of a drive control apparatus of the drive assist system according to the example embodiment of the technology.

As illustrated in FIG. 2, the drive assist apparatus 100 according to the first example embodiment includes a processor 110 and a memory 120.

The processor 110 may perform a general control of the drive assist apparatus 100 in accordance with a control program. The control program may be stored in the memory 120 which will be described later.

According to the first example embodiment, the processor 110 may execute processes to be performed by units including, without limitation, an information reception unit 111, a sleep determination unit 112, and a drive assist control unit 113 which will be described later.

The memory 120 may include, for example but not limited to, a read-only memory (ROM) and a random-access memory (RAM). The ROM may have, for example but not limited to, the above-described control program stored therein. The RAM may have, for example but not limited to, various pieces of data stored therein.

According to the first example embodiment, for example, information from the occupant monitoring apparatus 10 and any other suitable information may be stored in the RAM.

[Configuration of Processor 110]

As illustrated in FIG. 2, the processor 110 may include the information reception unit 111, the sleep determination unit 112, and the drive assist control unit 113.

The information reception unit 111 may receive, from the occupant monitoring apparatus 10, information regarding the physical state of the occupant of the vehicle including, without limitation, a behavior, a facial expression, and a health condition of the occupant. In the first example embodiment, the information reception unit 111 may receive information regarding the sleep state including, without limitation, the sleep duration and the quality of sleep of the driver, for example.

The information reception unit 111 may store the information received from the occupant monitoring apparatus 10 in the RAM in the memory 120.

Upon receiving, from the determination apparatus 20, information that the vehicle is in the stopped state, the sleep determination unit 112 may determine the sleep state including, without limitation, the sleep duration and the quality of sleep of the driver on the basis of the monitoring information acquired by the occupant monitoring apparatus 10 and stored in the RAM in the memory 120.

For example, in a case where the sleep duration (accumulated sleep duration) is used as an index of determination of the sleep state, the sleep determination unit 112 may determine a depth of sleep on the basis of whether the sleep duration in the acquired information is longer than a predetermined time.

For example, the above-mentioned "predetermined time" may be set from accumulated sleep duration inside the vehicle of each day measured for each driver as described in FIG. 3, on the basis of the monitoring information acquired by the occupant monitoring apparatus 10 for a week.

Referring to an example in FIG. 3, in one example, "predetermined time" may be set from an average value of values of the accumulated sleep duration inside the vehicle of respective days measured for each driver. In another example, the "predetermined time" may be set as a peak time in a distribution of the accumulated sleep duration inside the vehicle of each day measured for each driver.

Note that, although FIG. 3 presents an example only for a particular person, similar data may need to be prepared for other occupants who may possibly drive the vehicle.

In a case where the quality of sleep is used as the index of the determination of the sleep state, the sleep determination unit 112 may determine the depth of sleep on the basis of whether the quality of sleep of the driver is at a predetermined level or higher. The information regarding the level of the quality of sleep of the driver may be acquired from the acquired information regarding the quality of sleep such as the number of times of rolling while sleeping, the REM sleep state, or the non-REM state.

The above-mentioned "predetermined level" may be determined using information already known as knowledge as a reference.

The drive assist control unit 113 may appropriately control the driving operation restriction apparatus 40 on the basis of a determination result obtained by the sleep determination unit 112 in a case where the vehicle is in the stopped state.

[Process of Drive Assist Apparatus 100]

Figure 4:
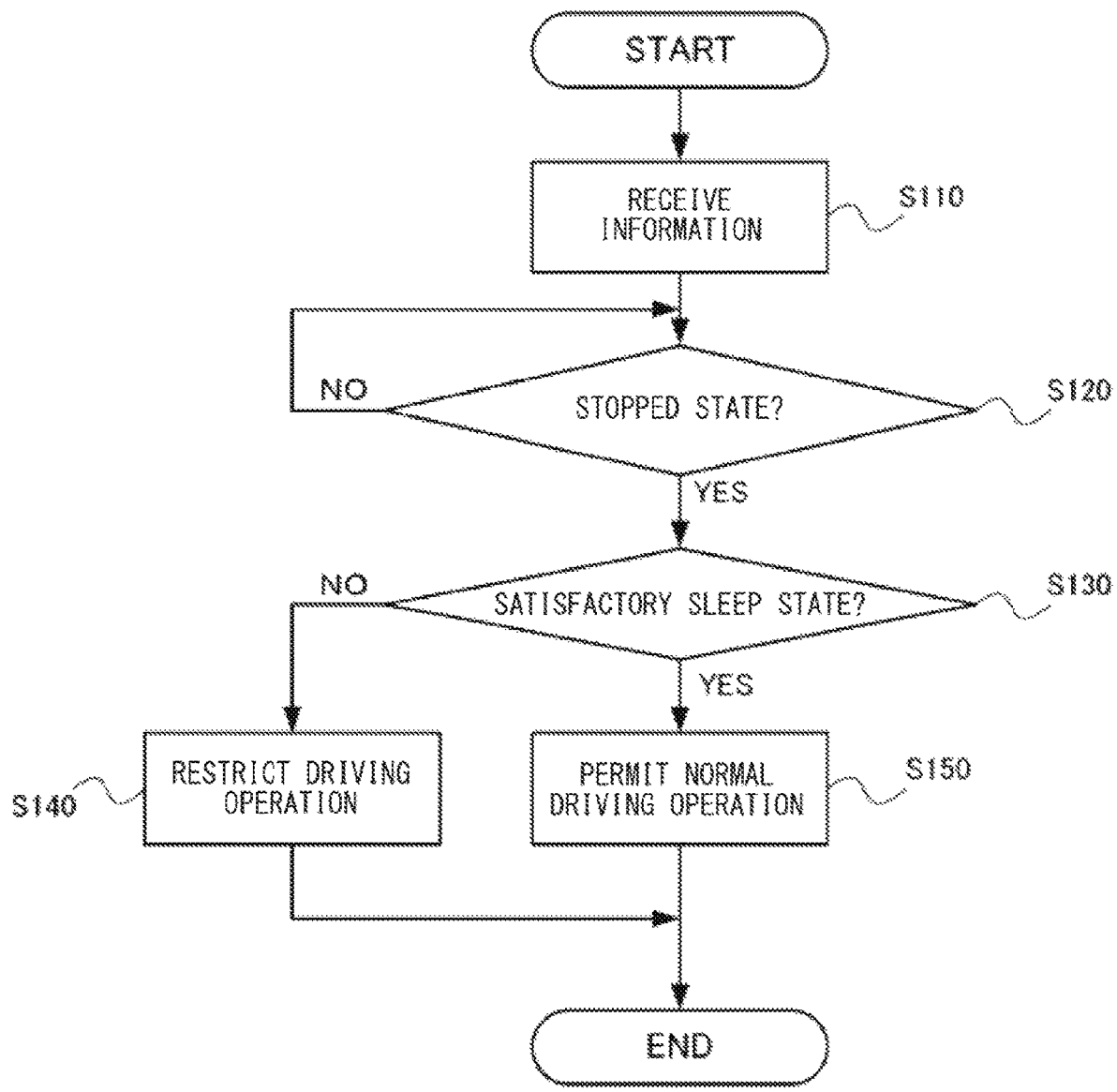
FIG. 4 is a flowchart illustrating an example of a process to be performed by the drive assist system according to the example embodiment of the technology.

Referring to FIG. 4, a process to be performed by the drive assist apparatus 100 according to the first example embodiment is described.

The information reception unit 111 of the drive assist apparatus 100 may receive occupant monitoring information from the occupant monitoring apparatus 10 (step S110).

Further, the information reception unit 111 may store the occupant monitoring information received from the occupant monitoring apparatus 10 in the RAM in the memory 120.

The sleep determination unit 112 of the drive assist apparatus 100 may determine whether the sleep determination unit 112 has received, from the determination apparatus 20, information that the vehicle is in the stopped state (step S120). Further, in a case where the sleep determination unit 112 determines that the sleep determination unit 112 has not received, from the determination apparatus 20, the information that the vehicle is in the stopped state (NO in step S120), the process may be caused to return to step S120, and the drive assist apparatus 100 may transition to a standby mode.

In a case where the sleep determination unit 112 determines that the sleep determination unit 112 has received, from the determination apparatus 20, the information that the vehicle is in the stopped state (YES in step S120), the sleep determination unit 112 may acquire, for example, information for determining the sleep state including the sleep duration and the quality of sleep of the driver from the information stored in the RAM in the memory 120, and determine whether the sleep state of the driver is satisfactory (step S130).

In a case where the sleep determination unit 112 determines that the sleep state of the driver is satisfactory (YES in step S130), the sleep determination unit 112 may supply the information that the sleep state of the driver is satisfactory to the drive assist control unit 113.

Further, the drive assist control unit 113, which has received the information from the sleep determination unit 112, may permit the driver to perform a normal driving operation (step S150).

In a case where the sleep determination unit 112 determines that the sleep state of the driver is not satisfactory (NO in step S130), the sleep determination unit 112 may supply the information that the sleep state of the driver is not satisfactory to the drive assist control unit 113.

Further, the drive assist control unit 113, which has received the information from the sleep determination unit 112, may perform a control of appropriately restricting the driving operation performed by the driver (step S140).

Example Workings and Example Effects

As described above, in the drive assist system 1 according to the first example embodiment, the processor 110 of the drive assist apparatus 100 may perform a control of appropriately restricting the driving operation performed by the driver, on the basis of the information at least regarding the sleep duration and the quality of sleep of the driver among the occupants of the vehicle in a case where the information from the determination apparatus 20 indicates that the vehicle is in the stopped state.

That is, in a case where the sleep state of the driver is not satisfactory, it is highly possible that safe traveling of the vehicle is disturbed.

To address this, the processor 110 of the drive assist apparatus 100 may determine at least the sleep state of the driver in a case where the information from the determination apparatus 20 indicates that the vehicle is in the stopped state. In a case where the sleep state of the driver is not satisfactory, the processor 110 may restrict the driving operation performed by the driver that causes an abrupt state change within a certain period of time. Non-limiting examples of such a driving operation may include sudden acceleration and sudden turning.

As a result, it is possible to perform appropriate drive assistance for safe traveling of the vehicle.

Further, the processor 110 of the drive assist apparatus 100 may set the predetermined time from the accumulated sleep duration in the vehicle measured for each driver, on the basis of the monitoring information acquired by the occupant monitoring apparatus 10.

This makes it possible to determine the sleep state of each driver using, as a reference, the predetermined time for each occupant who drives the vehicle, allowing for highly accurate determination.

As a result, it is possible to perform appropriate drive assistance for safe traveling of the vehicle.

Further, in a case where the occupant monitoring apparatus 10 includes both the optical camera and the near-infrared ray camera, it is possible to acquire an image of the occupant at any time of day and night.

This makes it substantially constantly possible to precisely acquire information regarding the sleep state at least of the driver among the occupants. As a result, it is possible to perform an appropriate drive assistance control.

Second Example Embodiment

Referring to FIGS. 5 to 8, a drive assist system 1A according to a second example embodiment of the technology is described.

[Configuration of Drive Assist System 1A]

Figure 5:
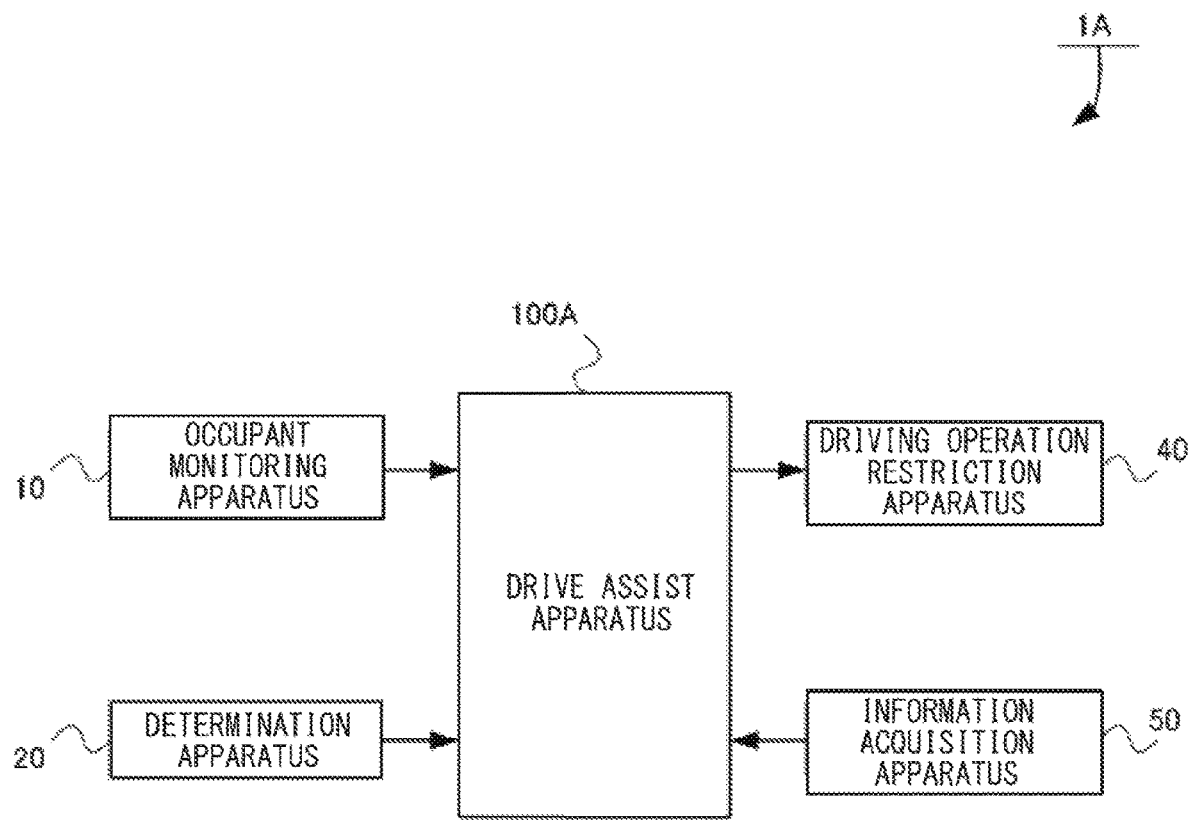
FIG. 5 is a diagram illustrating an example of a configuration of a drive assist system according to an example embodiment of the technology.

As illustrated in FIG. 5, the drive assist system 1A according to the second example embodiment may include the occupant monitoring apparatus 10, the determination apparatus 20, the driving operation restriction apparatus 40, an information acquisition apparatus 50, and a drive assist apparatus 100A.

Note that the components denoted with the same referential signs as those in the first example embodiment may serve as the same, and are therefore not described further in detail here.

The information acquisition apparatus 50 may be provided inside or outside of the vehicle. The information acquisition apparatus 50 acquires, for example, biometric information of the occupant.

Non-limiting examples of the biometric information of the occupant may include vital data of each occupant.

Non-limiting examples of the information acquisition apparatus 50 provided inside the vehicle may include an apparatus mounted on the vehicle and an apparatus worn or carried by the occupant, such as a smartwatch or a smartphone.

Non-limiting examples of the information acquisition apparatus 50 provided outside the vehicle may include a fixed apparatus and a movable apparatus provided in the occupant's home.

Non-limiting examples of the fixed apparatus may include an apparatus provided on a ceiling or a wall of a bedroom, a stationary apparatus, and an apparatus embedded in a bed mattress or the like.

Non-limiting examples of the movable apparatus may include an apparatus mounted on a robot or the like.

Non-limiting examples of information to be obtained from the information acquisition apparatus 50 may include a heart rate, blood-oxygen saturation, heart rate variability, a respiratory rate, a body temperature, a blood pressure, a hemoglobin level, an activity amount, the number of times of rolling while sleeping, a sleep state, and sleep duration.

Here, for example, the number of times of rolling while sleeping, a REM sleep state, and a non-REM state may serve as example indices used for detecting the sleep state including the quality of sleep.

In a case where determination result obtained by the determination apparatus 20 indicates that the vehicle is in the stopped state, the drive assist apparatus 100A may determine whether the sleep duration at least of the driver among the occupants is less than the predetermined time and whether the quality of sleep at least of the driver among the occupants is lower than the predetermined level, on the basis of the monitoring information acquired by the occupant monitoring apparatus 10, acquisition information acquired by the information acquisition apparatus 50, or both. Further, the drive assist apparatus 100A may perform a control of appropriately restricting the driving operation performed by the driver on the basis of a result of the determination.

According to the second example embodiment, in a case where the sleep duration at least of the driver among the occupants of the vehicle is determined as being less than the predetermined time and where the quality of sleep at least of the driver among the occupants of the vehicle is determined as being lower than the predetermined level, the drive assist apparatus 100A may perform a control of restricting sudden acceleration accompanied by an abrupt state change within a certain time period.

Here, non-limiting examples of the driving operation restriction apparatus 40 that restricts the sudden acceleration of the vehicle may include an acceleration limiter. For example, the drive assist apparatus 100A may perform a control of lowering an upper-limit speed of the acceleration limiter. After the speed of the vehicle reaches the set upper-limit speed, the drive assist apparatus 100A may perform a control of preventing acceleration even if the driver performs an acceleration operation.

Details will be described later.

[Configuration of Drive Assist Apparatus 100A]

Figure 6:
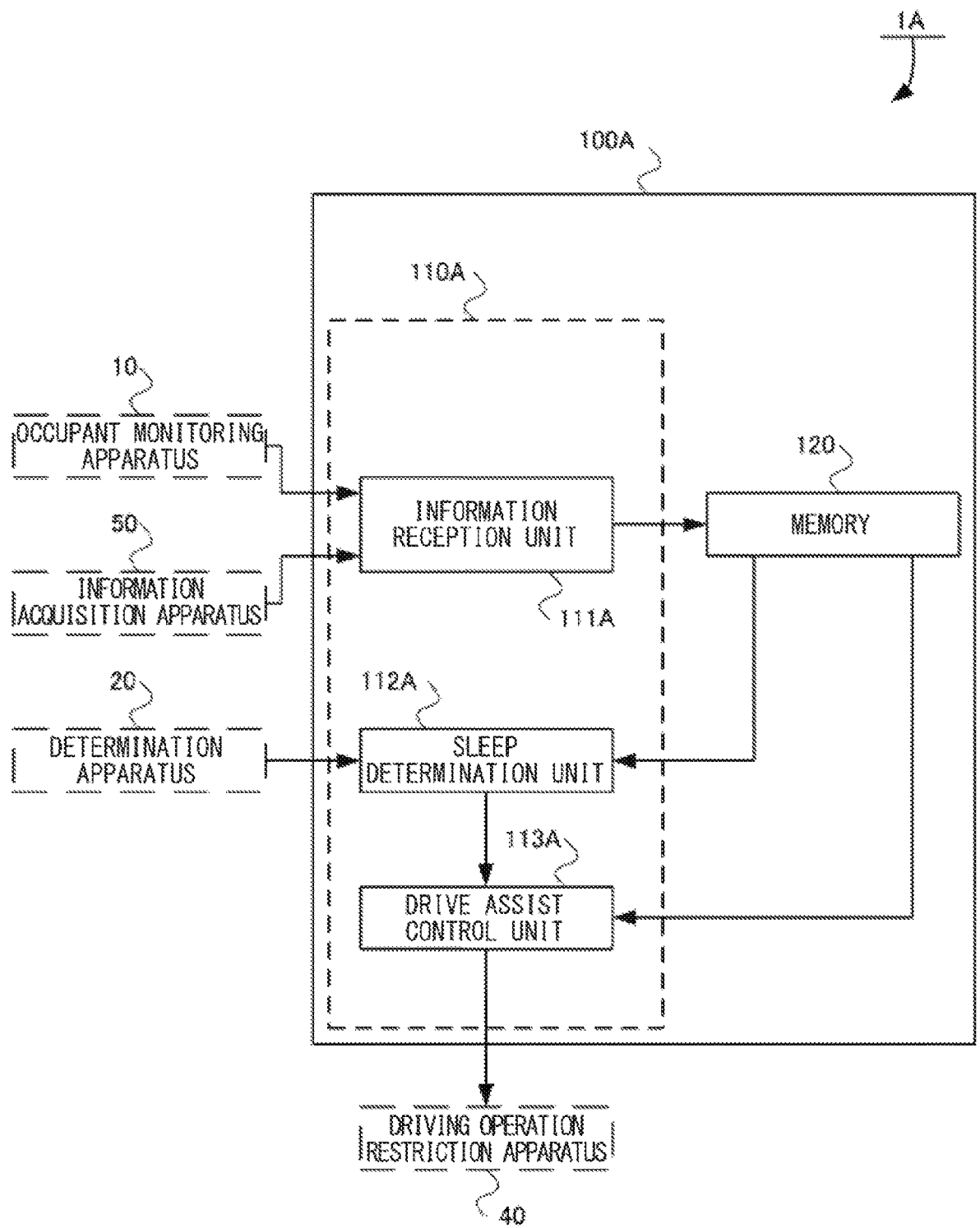
FIG. 6 is a diagram illustrating an example of a configuration of a drive control apparatus of the drive assist system according to the example embodiment of the technology.

As illustrated in FIG. 6, the drive assist apparatus 100A may include a processor 110A and the memory 120. The processor 110A will be described in detail later.

[Configuration of Processor 110A]

As illustrated in FIG. 6, the processor 110A may include an information reception unit 111A, a sleep determination unit 112A, and a drive assist control unit 113A.

The information reception unit 111A may receive, from the occupant monitoring apparatus 10, information regarding the physical state of the occupant of the vehicle including, without limitation, the behavior, the facial expression, and the health condition of the occupant.

The information reception unit 111A may also receive, from the information acquisition apparatus 50, information regarding, for example but not limited to, the heart rate, the blood-oxygen saturation, the heart rate variability, the respiratory rate, the body temperature, the blood pressure, the hemoglobin level, the activity amount, the number of times of rolling while sleeping, the sleep state, and the sleep duration.

In the second example embodiment, the information reception unit 111A may receive information regarding the sleep state including, without limitation, the sleep duration and the quality of sleep of the driver, for example.

Upon receiving, from the determination apparatus 20, information that the vehicle is in the stopped state, the sleep determination unit 112A may determine the sleep state including, without limitation, the sleep duration and the quality of sleep of the driver on the basis of the monitoring information acquired by the occupant monitoring apparatus 10 and stored in the RAM in the memory 120, the acquisition information acquired by the information acquisition apparatus 50, or both.

For example, in a case where the sleep duration (accumulated sleep duration) is used as an index of determination of the sleep state, the sleep determination unit 112A may determine the sleep state on the basis of whether the sleep duration in the acquired information is longer than a predetermined time.

According to the second example embodiment, the information acquisition apparatus 50 may be provided in addition to the occupant monitoring apparatus 10. This makes it possible to obtain the sleep state of the occupant, including the driver, inside and outside the vehicle.

The above-mentioned "sleep duration (accumulated sleep duration)" may refer to sleep duration (accumulated sleep duration) inside and outside the vehicle for each day.

For example, the above-mentioned "predetermined time" may be set from accumulated sleep duration inside and outside the vehicle of each day measured for each driver as described in FIG. 7, on the basis of the monitoring information acquired by the occupant monitoring apparatus 10 for a week, the acquisition information acquired by the information acquisition apparatus 50 for a week, or both.

In one example, referring to an example in FIG. 7, "predetermined time" may be set from an average value of values of the accumulated sleep duration inside and outside the vehicle of respective days measured for each driver. In another example, the "predetermined time" may be set as a peak time in a distribution of the accumulated sleep duration inside and outside the vehicle of each day measured for each driver.

Note that, although FIG. 7 presents an example only for a particular person, similar data may need to be prepared for other occupants who may possibly drive the vehicle. In a case where the determination result obtained by the determination apparatus 20 indicates that the vehicle is in the stopped state, the drive assist control unit 113A may perform a control of restricting sudden acceleration of the vehicle accompanied by an abrupt state change within a certain time period, on the basis of a determination result obtained by the sleep determination unit 112.

For example, in a case: where the determination information from the determination apparatus 20 is information indicating the stopped state of the vehicle; where the sleep duration at least of the driver among the occupants of the vehicle is determined as being less than the predetermined time; and where the quality of sleep at least of the driver among the occupants of the vehicle is determined as lower than the predetermined level, the drive assist control unit 113A may supply a control signal to the acceleration limiter serving as the driving operation restriction apparatus 40 to thereby restrict the sudden acceleration of the vehicle.

[Process of Drive Assist Apparatus 100A]

Figure 8:
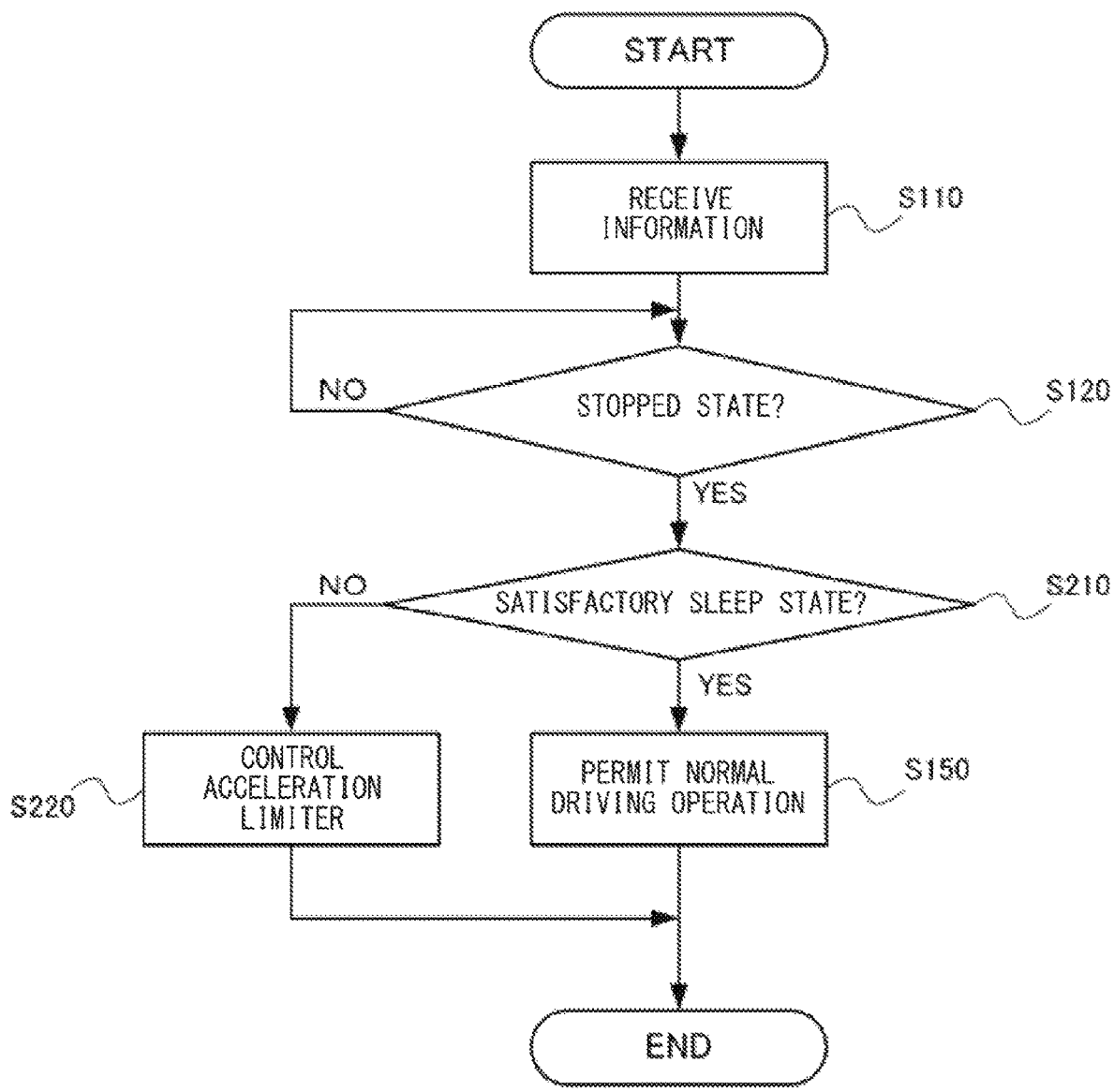
FIG. 8 is a flowchart illustrating an example of a process to be performed by the drive assist system according to the example embodiment of the technology.

Referring to FIG. 8, a process to be performed by the drive assist apparatus 100A according to the second example embodiment is described.

The information reception unit 111A of the drive assist apparatus 100A may receive the occupant monitoring information from the occupant monitoring apparatus 10 and the acquisition information from the information acquisition apparatus 50 (step S110).

Further, the information reception unit 111A may store the occupant monitoring information received from the occupant monitoring apparatus 10 and the acquisition information received from the information acquisition apparatus 50 in the RAM in the memory 120.

The sleep determination unit 112A of the drive assist apparatus 100A may determine whether the sleep determination unit 112A has received, from the determination apparatus 20, information that the vehicle is in the stopped state (step S120). Further, in a case where the sleep determination unit 112A determines that the sleep determination unit 112 has not received, from the determination apparatus 20, the information that the vehicle is in the stopped state (NO in step S120), the process may be caused to return to step S120, and the drive assist apparatus 100A may transition to a standby mode.

In a case where the sleep determination unit 112A determines that the sleep determination unit 112A has received, from the determination apparatus 20, the information that the vehicle is in the stopped state (YES in step S120), the sleep determination unit 112A may acquire, for example, information for determining the sleep state from the information stored in the RAM in the memory 120, and determine whether the sleep duration at least of the driver among the occupants of the vehicle is less than the predetermined time and whether the quality of sleep at least of the driver among the occupants of the vehicle is lower than the predetermined level (step S210).

In a case where the sleep determination unit 112A determines that the sleep duration of the driver is the predetermined time or more and that the quality of sleep of the driver is the predetermined level or higher (YES in step S210), the sleep determination unit 112A may supply the information that the sleep duration of the driver is the predetermined time or more and that the quality of sleep of the driver is the predetermined level or higher to the drive assist control unit 113A.

Further, the drive assist control unit 113A, which has received the information from the sleep determination unit 112A, may permit the driver to perform the normal driving operation (step S150).

In a case where the sleep determination unit 112A determines that the sleep duration of the driver is less than the predetermined time and that the quality of sleep of the driver is lower than the predetermined level (NO in step S210), the sleep determination unit 112A may supply the information that the sleep duration of the driver is less than the predetermined time and that the quality of sleep is lower than the predetermined level to the drive assist control unit 113A.

Further, the drive assist control unit 113A, which has received the information from the sleep determination unit 112A, may supply a control signal to the acceleration limiter serving as the driving operation restriction apparatus 40 to thereby restrict the sudden acceleration of the vehicle (step S220).

Example Workings and Example Effects

As described above, the processor 110A of the drive assist apparatus 100A in the drive assist system 1A according to the second example embodiment may determine the sleep state of the driver on the basis of the monitoring information acquired by the occupant monitoring apparatus 10, the acquisition information acquired by the information acquisition apparatus 50, or both. In a case where the sleep duration of the driver is determined as being less than the predetermined time and where the quality of sleep of the driver is determined as being lower than the predetermined level, the processor 110A may perform a control of restricting sudden acceleration of the vehicle accompanied by an abrupt state change within a certain time period.

That is, in a case of driving of the vehicle by a driver having an unsatisfactory sleep state, it can be considered that the determination ability at the time of traveling is low.

Therefore, in the case where the sleep state of the driver is not satisfactory, the control of restricting the sudden acceleration of the vehicle accompanied by an abrupt state change within a certain time period is performed. As a result, it is possible to perform appropriate drive assistance for safe traveling, for example, even in a case where the driver is in a drowsy state.

In addition, the drive assist system 1A according to the second embodiment may further include the information acquisition apparatus 50 that acquires the biometric information, including the sleep information, of the occupant inside and outside the vehicle. The processor 110A of the drive assist apparatus 100A may determine the sleep state of the driver on the basis of the monitoring information acquired by the occupant monitoring apparatus 10, the acquisition information acquired by the information acquisition apparatus 50, or both.

That is, further including the information acquisition apparatus 50 makes it possible to also acquire the sleep state of the driver outside the vehicle. Accordingly, it is substantially constantly possible to perform sleep state determination with higher accuracy.

As a result, it is possible to perform appropriate drive assistance for safe traveling.

In addition, the processor 110A of the drive assist apparatus 100A may set the predetermined time from the accumulated sleep duration inside and outside the vehicle of each day measured for each driver, on the basis of the monitoring information acquired by the occupant monitoring apparatus 10, the acquisition information acquired by the information acquisition apparatus 50, or both.

That is, the predetermined time for each occupant who drives the vehicle may be set from the accumulated sleep duration not only inside but also outside the vehicle of each day measured for each driver. It is thus possible to determine the sleep state of each driver using the set predetermined time as a reference. This makes it possible to substantially constantly perform determination with high accuracy.

As a result, it is possible to perform appropriate drive assistance for safe traveling of the vehicle.

Third Example Embodiment

Figure 9:
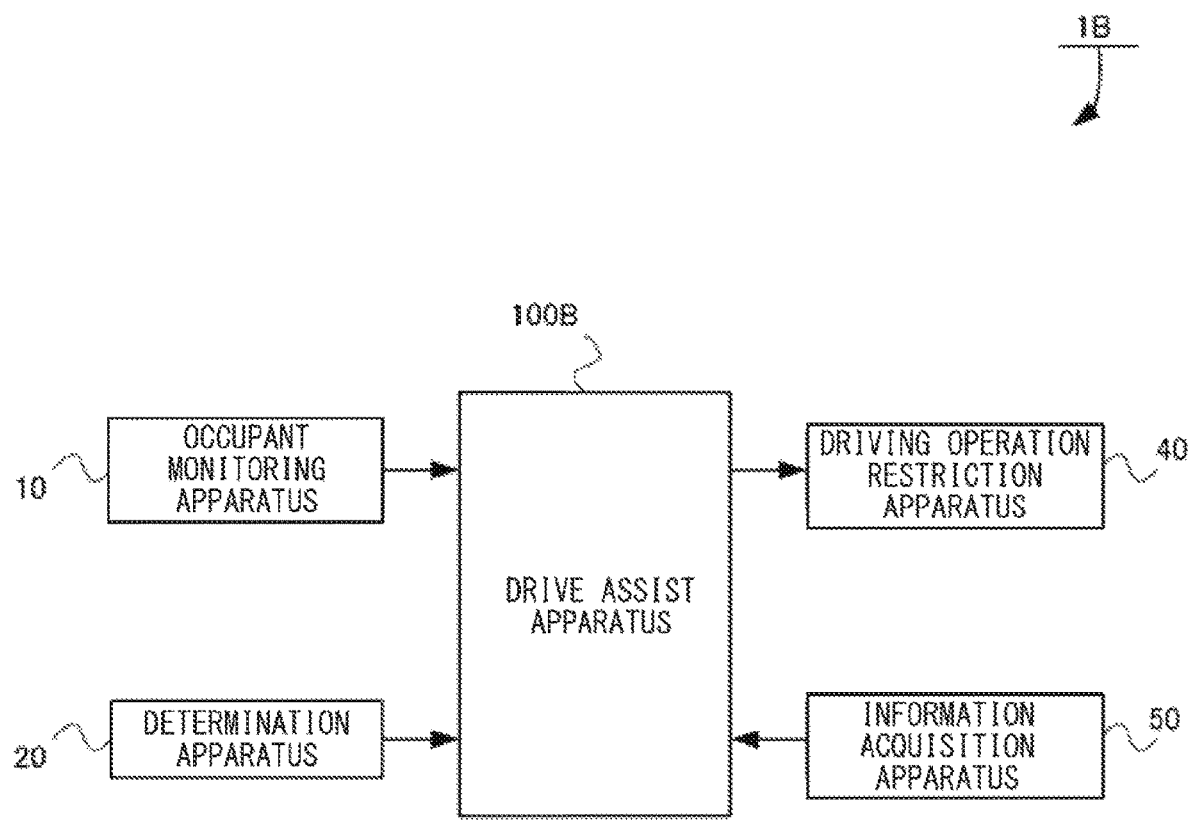
FIG. 9 is a diagram illustrating an example of a configuration of a drive assist system according to an example embodiment of the technology.
Figure 10:
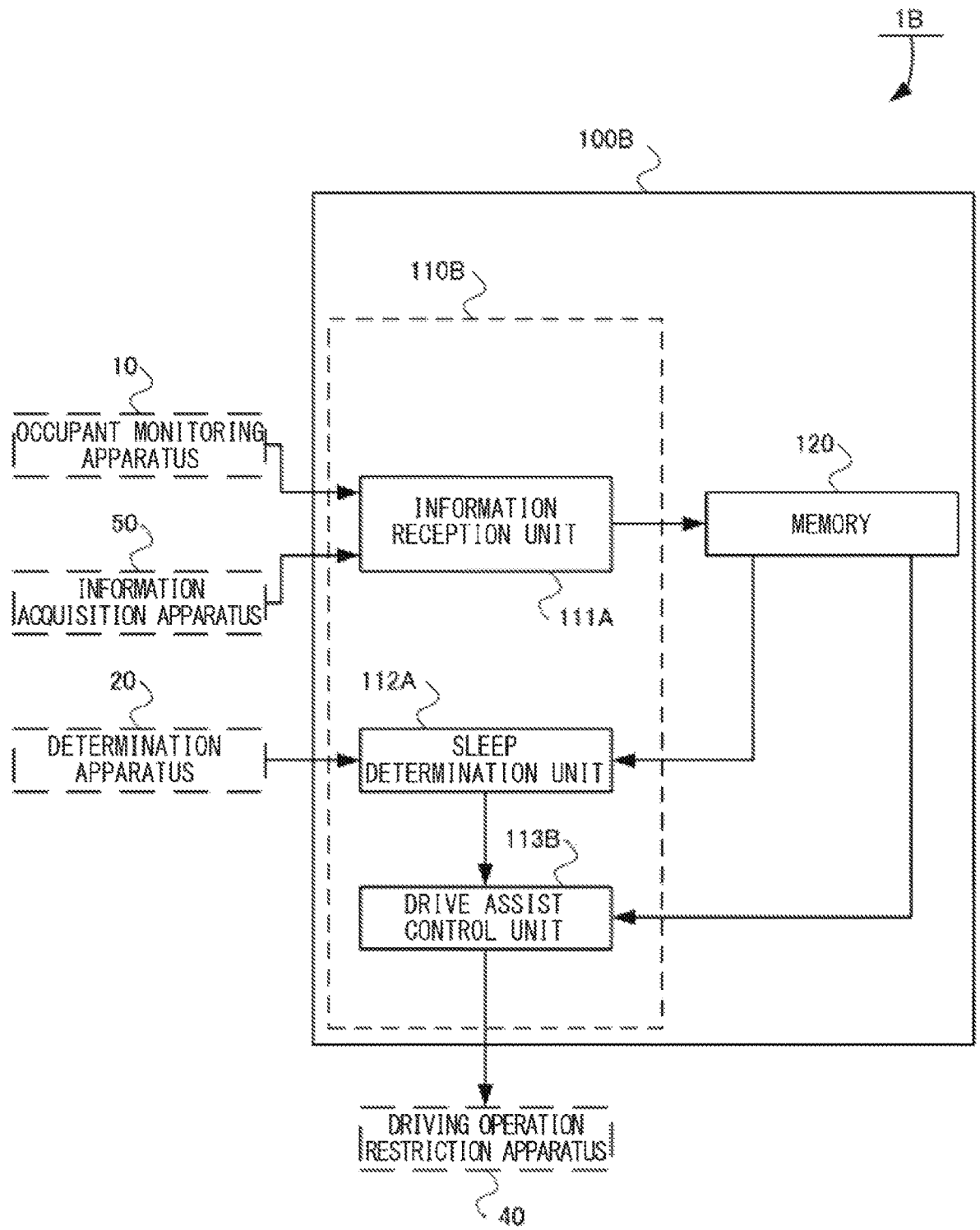
FIG. 10 is a diagram illustrating an example of a configuration of a drive control apparatus of the drive assist system according to the example embodiment of the technology.
Figure 11:
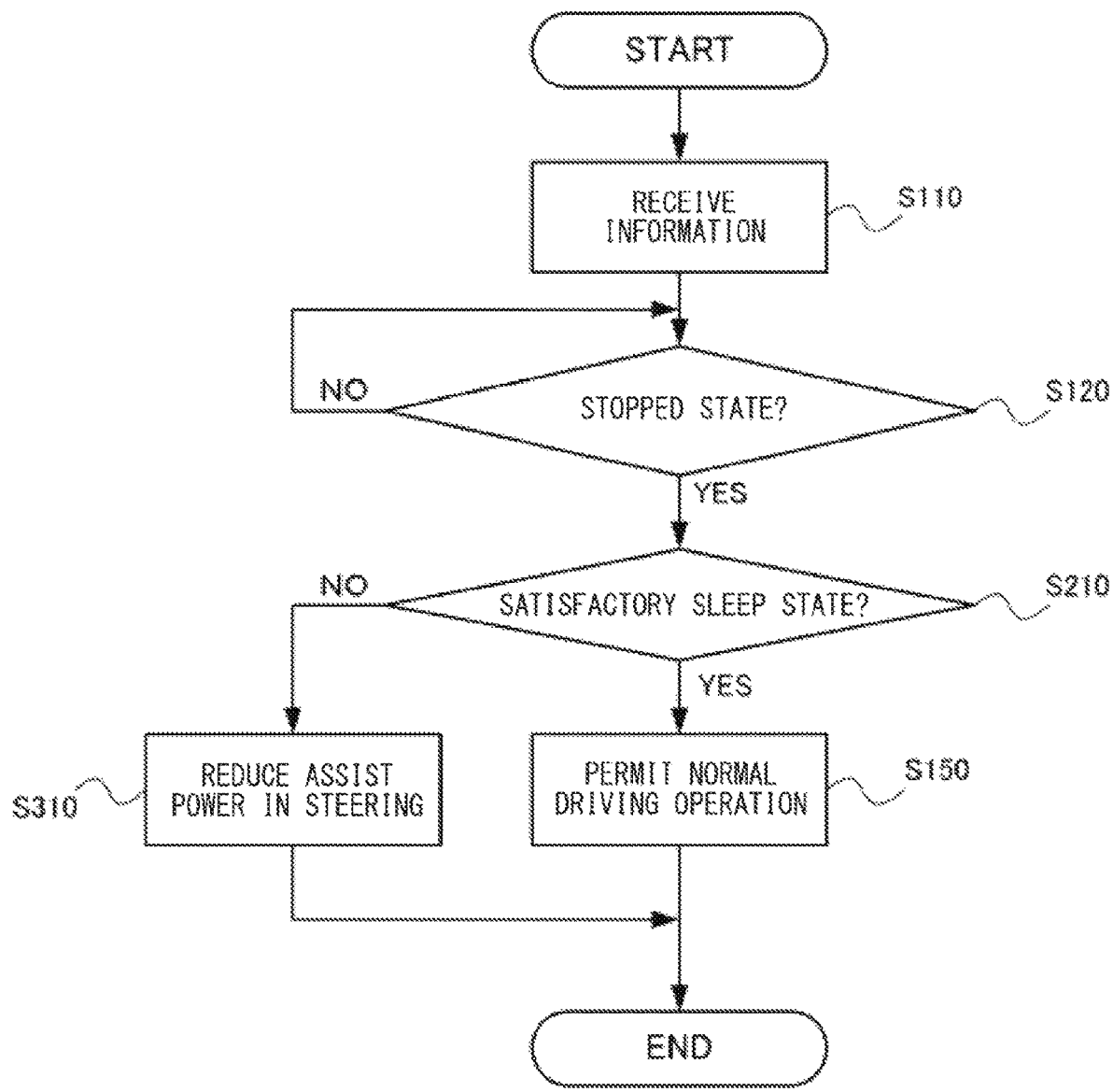
FIG. 11 is a flowchart illustrating an example of a process to be performed by the drive assist system according to the example embodiment of the technology.

Referring to FIGS. 9 to 11, a drive assist system 1B according to a third example embodiment of the technology is described.

[Configuration of Drive Assist System 1B]

As illustrated in FIG. 9, the drive assist system 1B according to the third example embodiment may include the occupant monitoring apparatus 10, the determination apparatus 20, the driving operation restriction apparatus 40, the information acquisition apparatus 50, and a drive assist apparatus 100B.

Note that the components denoted with the same referential signs as those in the first and the second example embodiments may serve as the same, and are therefore not described further in detail here.

In a case where the determination result obtained by the determination apparatus 20 indicates that the vehicle is in the stopped state, the drive assist apparatus 100B may determine whether the sleep duration at least of the driver among the occupants is less than the predetermined time and whether the quality of sleep at least of the driver among the occupants is lower than the predetermined level, on the basis of the monitoring information acquired by the occupant monitoring apparatus 10, the acquisition information acquired by the information acquisition apparatus 50, or both. Further, the drive assist apparatus 100B may perform a control of appropriately restricting the driving operation performed by the driver on the basis of a result of the determination.

According to the third example embodiment, in a case where the sleep duration at least of the driver among the occupants of the vehicle is determined as being less than the predetermined time and where the quality of sleep at least of the driver among the occupants of the vehicle is determined as being lower than the predetermined level, the drive assist apparatus 100B may perform a control of restricting sudden turning, performed by the driver, accompanied by an abrupt state change within a certain time period.

Here, non-limiting examples of the driving operation restriction apparatus 40 that restricts the sudden turning of the vehicle may include a power steering apparatus. For example, the drive assist apparatus 100B may perform a control of reducing assist power in a case where an acceleration sensor included in the power steering apparatus detects sudden turning in steering when a steering operation is performed.

Details will be described later.

[Configuration of Drive Assist Apparatus 100B]

As illustrated in FIG. 10, the drive assist apparatus 100B may include a processor 110B and the memory 120. The processor 110B will be described in detail later.

[Configuration of Processor 110B]

As illustrated in FIG. 10, the processor 110B may include the information reception unit 111A, the sleep determination unit 112A, and a drive assist control unit 113B.

In a case: where the determination result obtained by the determination apparatus 20 indicates that the vehicle is in the stopped state; and where the sleep determination unit 112A determines that the sleep duration at least of the driver among the occupants of the vehicle is less than the predetermined time and that the quality of sleep at least of the driver among the occupants of the vehicle is lower than the predetermined level, the drive assist control unit 113B may perform a control of restricting sudden turning, performed by the driver, accompanied by an abrupt state change within a certain time period.

[Process of Drive Assist Apparatus 100B]

Referring to FIG. 11, a process to be performed by the drive assist apparatus 100B according to the third example embodiment is described.

The information reception unit 111A of the drive assist apparatus 100B may receive the monitoring information from the occupant monitoring apparatus 10 and the acquisition information from the information acquisition apparatus 50 (step S110).

Further, the information reception unit 111A may store the occupant monitoring information received from the occupant monitoring apparatus 10 and the acquisition information received from the information acquisition apparatus 50 in the RAM in the memory 120.

The sleep determination unit 112A of the drive assist apparatus 100B may determine whether the sleep determination unit 112A has received, from the determination apparatus 20, information that the vehicle is in the stopped state (step S120). Further, in a case where the sleep determination unit 112A determines that the sleep determination unit 112A has not received, from the determination apparatus 20, the information that the vehicle is in the stopped state (NO in step S120), the process may be caused to return to step S120, and the drive assist apparatus 100B may transition to a standby mode.

In a case where the sleep determination unit 112A determines that the sleep determination unit 112A has received, from the determination apparatus 20, the information that the vehicle is in the stopped state (YES in step S120), the sleep determination unit 112A may acquire, for example, information for determining the sleep state from the information stored in the RAM in the memory 120, and determine whether the sleep duration at least of the driver among the occupants of the vehicle is less than the predetermined time and whether the quality of sleep at least of the driver among the occupants of the vehicle is lower than the predetermined level (step S210).

In a case where the sleep determination unit 112A determines that the sleep duration of the driver is the predetermined time or more and that the quality of sleep of the driver is the predetermined level or higher (YES in step S210), the sleep determination unit 112A may supply the information that the sleep duration of the driver is the predetermined time or more and that the quality of sleep of the driver is the predetermined level or higher to the drive assist control unit 113B.

Further, the drive assist control unit 113B, which has received the information from the sleep determination unit 112A, may permit the driver to perform the normal driving operation (step S150).

In a case where the sleep determination unit 112A determines that the sleep duration of the driver is less than the predetermined time and that the quality of sleep of the driver is lower than the predetermined level (NO in step S210), the sleep determination unit 112A may supply the information that the sleep duration of the driver is less than the predetermined time and that the quality of sleep of the driver is lower than the predetermined level to the drive assist control unit 113B.

Further, the drive assist control unit 113B, which has received the information from the sleep determination unit 112A, may perform a control of restricting sudden turning, performed by the driver, accompanied by an abrupt state change within a certain time period, for example, a control of reducing assist power in steering (step S310).

Example Workings and Example Effects

As described above, the processor 110B of the drive assist apparatus 100B in the drive assist system 1B according to the third example embodiment may determine the sleep state of the driver on the basis of the monitoring information acquired by the occupant monitoring apparatus 10, the acquisition information acquired by the information acquisition apparatus 50, or both. In a case where the sleep duration of the driver is determined as being less than the predetermined time and where the quality of sleep of the driver is determined as being lower than the predetermined level, the processor 110B may perform a control of restricting sudden turning, performed by the driver, accompanied by an abrupt state change within a certain time period.

That is, in a case of driving of the vehicle by a driver having an unsatisfactory sleep state, it can be considered that the determination ability at the time of traveling is low.

Therefore, in the case where the sleep state of the driver is not satisfactory, the control of restricting sudden turning, performed by the driver, accompanied by an abrupt state change within a certain time period may be performed. As a result, it is possible to perform appropriate drive assistance for safe traveling, for example, even in a case where the driver is in a drowsy state.

Fourth Example Embodiment

Figure 12:
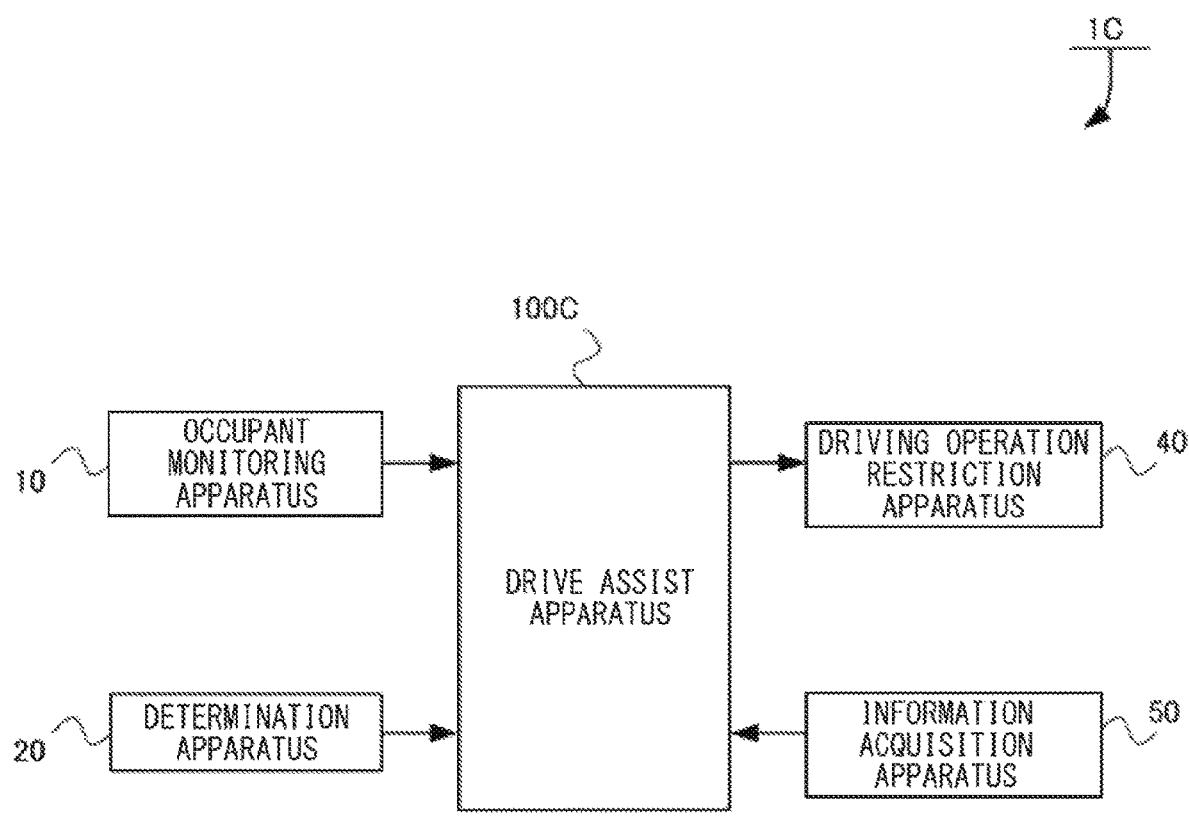
FIG. 12 is a diagram illustrating an example of a configuration of a drive assist system according to an example embodiment of the technology.
Figure 13:
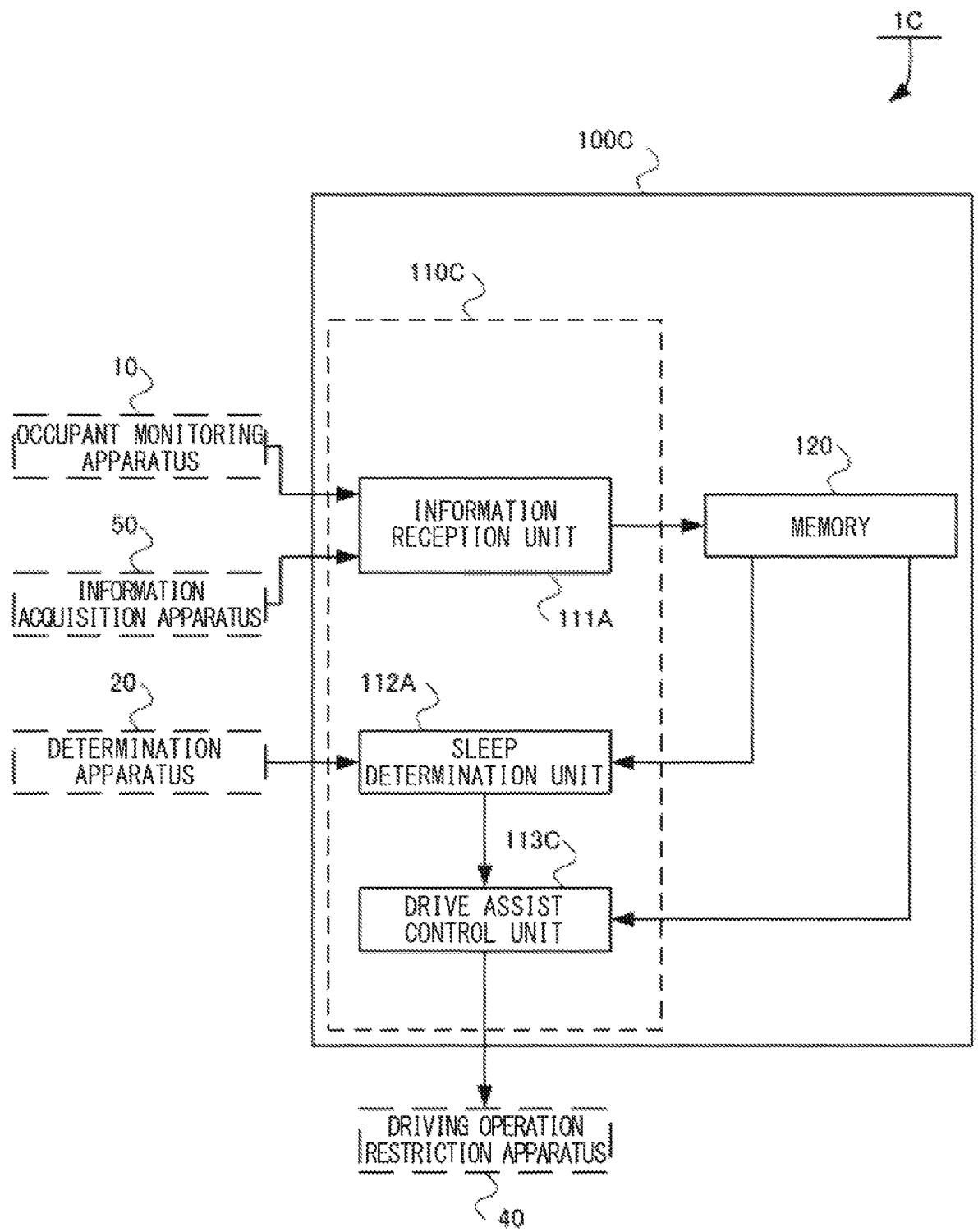
FIG. 13 is a diagram illustrating an example of a configuration of a drive control apparatus of the drive assist system according to the example embodiment of the technology.
Figure 14:
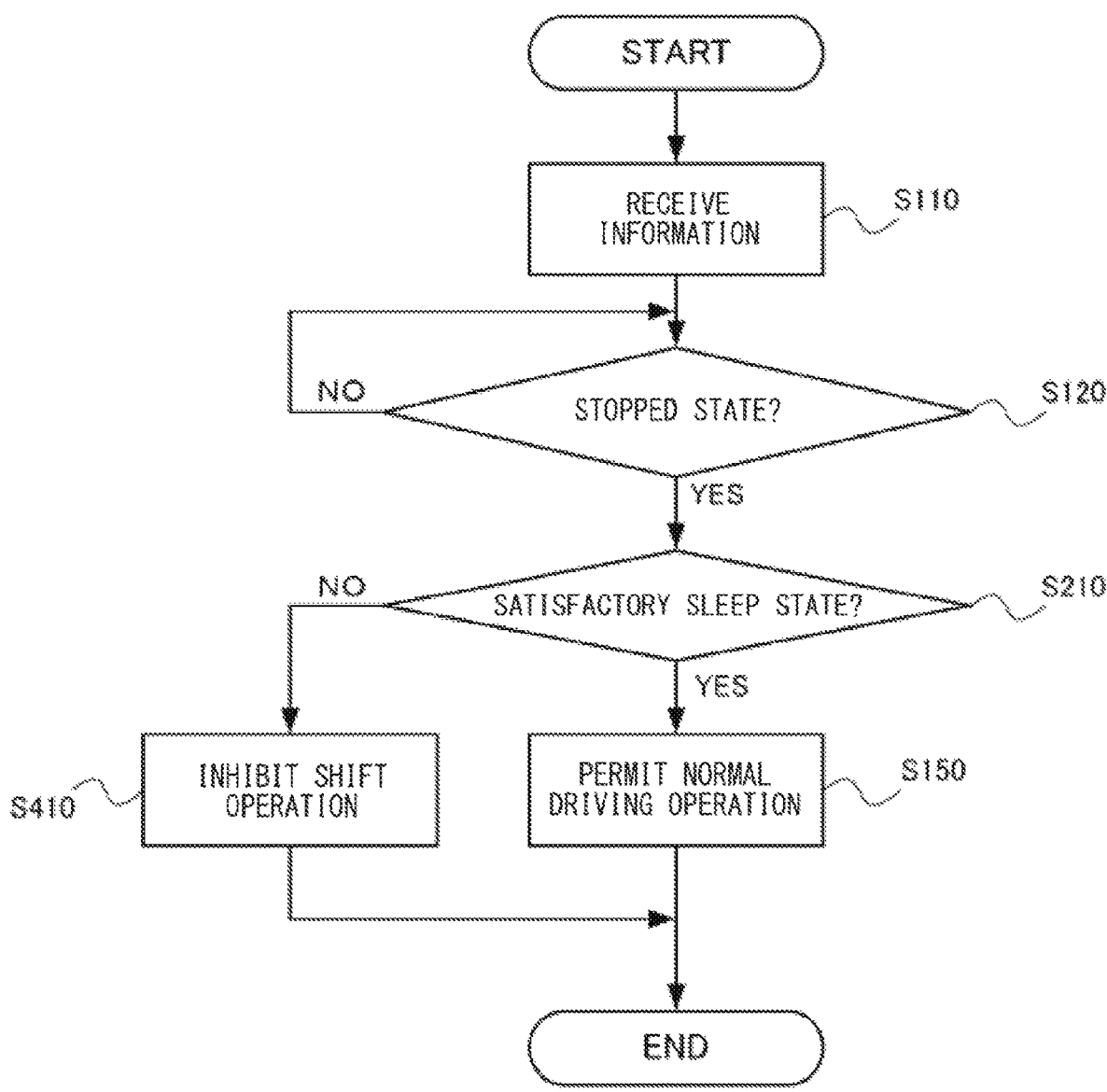
FIG. 14 is a flowchart illustrating an example of a process to be performed by the drive assist system according to the example embodiment of the technology.

Referring to FIGS. 12 to 14, a drive assist system 1C according to a fourth example embodiment of the technology is described.
[Configuration of Drive Assist System 1C]
As illustrated in FIG. 12, the drive assist system 1C according to the fourth example embodiment may include the occupant monitoring apparatus 10, the determination apparatus 20, the driving operation restriction apparatus 40, the information acquisition apparatus 50, and a drive assist apparatus 100C.

Note that the components denoted with the same referential signs as those in the first to the third example embodiments may serve as the same, and are therefore not described further in detail here.

In a case where the determination information obtained by the determination apparatus 20 indicates that the vehicle is in the stopped state, the drive assist apparatus 100C may determine whether the sleep duration at least of the driver among the occupants is less than the predetermined time and whether the quality of sleep at least of the driver among the occupants is lower than the predetermined level, on the basis of the monitoring information acquired by the occupant monitoring apparatus 10, the acquisition information acquired by the information acquisition apparatus 50, or both. Further, the drive assist apparatus 100C may perform a control of appropriately restricting the driving operation performed by the driver, on the basis of a result of the determination.

According to the fourth example embodiment, in a case where the sleep duration at least of the driver among the occupants of the vehicle is determined as being less than the predetermined time and where the quality of sleep at least of the driver among the occupants of the vehicle is determined as being lower than the predetermined level, the drive assist apparatus 100C may perform a control of restricting a shift operation, performed by the driver, which can cause an abrupt state change within a certain time period.

Here, non-limiting examples of the driving operation restriction apparatus 40 that restricts the shift operation may include a shift apparatus. For example, in a case where the driving operation restriction apparatus 40 is a shift apparatus having: a mode in which the maximum output is decreased (in a case of a vehicle with a turbocharger, a boost pressure is reduced) and fuel-economy-prioritized traveling is performed (i.e., an I mode); a mode adapted for high-speed traveling (i.e., an S mode); and a mode with an acceleration response higher than that in the S mode (i.e., an S # mode), the drive assist apparatus 100C may perform a control of fixing the shift position to the I mode.

Details will be described later.
[Configuration of Drive Assist Apparatus 100C]
As illustrated in FIG. 13, the drive assist apparatus 100C may include a processor 110C and the memory 120. The processor 110C will be described in detail later.
[Configuration of Processor 110C]
As illustrated in FIG. 13, the processor 110C may include the information reception unit 111A, the sleep determination unit 112A, and a drive assist control unit 113C.

In a case where the determination result obtained by the determination apparatus 20 indicates that the vehicle is in the stopped state, and where the determination result obtained by the sleep determination unit 112A indicates that the sleep duration at least of the driver among the occupants of the vehicle is less than the predetermined time and that the quality of sleep at least of the driver among the occupants of the vehicle is lower than the predetermined level, the drive assist control unit 113C may perform a control of restricting the shift operation, performed by the driver, which can cause an abrupt state change within a certain time period.
[Process of Drive Assist Apparatus 100C]
Referring to FIG. 14, a process to be performed by the drive assist apparatus 100C according to the fourth example embodiment is described.

The information reception unit 111A of the drive assist apparatus 100C may receive the monitoring information from the occupant monitoring apparatus 10 and the acquisition information from the information acquisition apparatus 50 (step S110).

Further, the information reception unit 111A may store the occupant monitoring information received from the occupant monitoring apparatus 10 and the acquisition information received from the information acquisition apparatus 50 in the RAM in the memory 120.

The sleep determination unit 112A of the drive assist apparatus 100C may determine whether the sleep determination unit 112A has received, from the determination apparatus 20, information that the vehicle is in the stopped state (step S120). Further, in a case where the sleep determination unit 112A determines that the sleep determination unit 112A has not received, from the determination apparatus 20, the information that the vehicle is in the stopped state (NO in step S120), the process may be caused to return to step S120, and the drive assist apparatus 100C may transition to a standby mode.

In a case where the sleep determination unit 112A determines that the sleep determination unit 112A has received, from the determination apparatus 20, the information that the vehicle is in the stopped state (YES in step S120), the sleep determination unit 112A may acquire, for example, information for determining the sleep state from the information stored in the RAM in the memory 120, and determine whether the sleep duration at least of the driver among the occupants of the vehicle is less than the predetermined time and whether the quality of sleep at least of the driver among the occupants of the vehicle is lower than the predetermined level (step S210).

In a case where the sleep determination unit 112A determines that the sleep duration of the driver is the predetermined time or more and that the quality of sleep of the driver is the predetermined level or higher (YES in step S210), the sleep determination unit 112A may supply the information that the sleep duration of the driver is the predetermined time or more and that the quality of sleep of the driver is the predetermined level or higher to the drive assist control unit 113C.

Further, the drive assist control unit 113C, which has received the information from the sleep determination unit 112A, may permit the driver to perform the normal driving operation (step S150).

In a case where the sleep determination unit 112A determines that the sleep duration of the driver is less than the predetermined time and that the quality of sleep of the driver is lower than the predetermined level (NO in step S210), the sleep determination unit 112A may supply the information that the sleep duration of the driver is less than the predetermined time and that the quality of sleep of the driver is lower than the predetermined level to the drive assist control unit 113C.

Further, the drive assist control unit 113C, which has received the information from the sleep determination unit 112A, may perform a control of fixing a shift position of the shift apparatus at a predetermined position to thereby inhibit the shift operation performed by the driver (step S410).

Example Workings and Example Effects

As described above, the processor 110C of the drive assist apparatus 100C in the drive assist system 1C according to the fourth example embodiment may determine the sleep state of the driver on the basis of the monitoring information acquired by the occupant monitoring apparatus 10, the acquisition information acquired by the information acquisition apparatus 50, or both. In a case where the sleep duration of the driver is determined as being less than the predetermined time and where the quality of sleep of the driver is determined as being lower than the predetermined level, the processor 110C may perform a control of restricting the shift operation, performed by the driver, which can cause an abrupt state change within a certain time period.

That is, in a case of driving of the vehicle by a driver having an unsatisfactory sleep state, it can be considered that the determination ability at the time of traveling is low.

Therefore, in the case where the sleep state of the driver is not satisfactory, the control of restricting the shift operation, performed by the driver, which can cause an abrupt state change within a certain time period is performed. As a result, it is possible to perform appropriate drive assistance for safe traveling, for example, even in a case where the driver is in a drowsy state.

[Modifications]

For example, the above example embodiments each have been described referring to a configuration in which the drive assist apparatus 100, 100A, 100B, or 100C is provided in the corresponding one of the drive assist systems 1, 1A, 1B, and 1C. However, this is non-limiting. One example embodiment may have a configuration in which the information acquired by the occupant monitoring apparatus 10 and the information acquired by the information acquisition apparatus 50 are transferred to a server coupled to the vehicle, and the control process performed by the drive assist apparatus 100, 100A, 100B, or 100C may be performed in the server.

This configuration may allow for quick processing of more information.

The first to the fourth example embodiments have been described referring to an example configuration in which the sleep determination unit 112 or 112A receives information from the determination apparatus 20, and determines whether the vehicle is in the stopped state. However, this is non-limiting. In one example, the drive assist control unit 113, 113A, 113B, or 113C may perform the above-described processes of information reception and determination.

Note that the drive assist system according to an embodiment of the technology may be implementable by: recording the process to be performed by the processor 110, 110A, 110B, or 110C in a recording medium readable by a computer system; and causing the processor 110, 110A, 110B, or 110C to read the program recorded in the recording medium to execute the program. The above-mentioned computer system encompasses an operating system (OS) and hardware such as a peripheral apparatus.

Further, two or more processors 110, 110A, 110B, or 110C may be provided. Further, two or more memories 120 may be provided.

In a case where the world wide web (WWW) system is used, the above-mentioned "computer system" encompasses a website provision environment or a website display environment. Further, the above-mentioned program may be transferred from the computer system having a storage device or the like holding the program to another computer system via a transfer medium or a transfer wave in the transfer medium. As used herein, the term "transfer medium" that transfers the program refers to a medium configured to transfer information, for example, a network (a communication network) such as the Internet or a communication line (a communication wire) such as a telephone line.

Moreover, the above-mentioned program may implement a portion of the above-described process to be performed by the drive assist system according to an embodiment of the technology.

Moreover, a combination of the above-mentioned program and another program pre-recorded in the computer system may implement the above-described process to be performed by the drive assist system according to an embodiment of the technology. That is, the above-mentioned program may be a differential file (a differential program).

Although some example embodiments of the technology have been described in detail with reference to the accompanying drawings, the specific configuration is not limited to those in the example embodiments described above. The technology includes designs, etc. not departing from the gist of the technology.

According to one or more example embodiments of the technology, the sleep state of the occupant, including the driver, inside the vehicle may be determined at the driving start timing of the vehicle. Accordingly, the one or more example embodiments of the technology achieve an effect of making it possible to perform appropriate drive assistance for safe traveling.

Each of the information reception unit 111 and 111A, the sleep determination unit 112 and 112A, the drive assist control unit 113, 113A, 113B, and 113C illustrated in FIGS. 2, 6, 10, and 13 is implementable by circuitry including at least one semiconductor integrated circuit such as at least one processor (e.g., a central processing unit (CPU)), at least one application specific integrated circuit (ASIC), and/or at least one field programmable gate array (FPGA). At least one processor is configurable, by reading instructions from at least one machine readable non-transitory tangible medium, to perform all or a part of functions of each of the information reception unit 111 and 111A, the sleep determination unit 112 and 112A, the drive assist control unit 113, 113A, 113B, and 113C illustrated in FIGS. 2, 6, 10, and 13. Such a medium may take many forms, including, but not limited to, any type of magnetic medium such as a hard disk, any type of optical medium such as a CD and a DVD, any type of semiconductor memory (i.e., semiconductor circuit) such as a volatile memory and a non-volatile memory. The volatile memory may include a DRAM and a SRAM, and the nonvolatile memory may include a ROM and a NVRAM. The ASIC is an integrated circuit (IC) customized to perform, and the FPGA is an integrated circuit designed to be configured after manufacturing in order to perform, all or a part of the functions of each of the information reception unit 111 and 111A, the sleep determination unit 112 and 112A, the drive assist control unit 113, 113A, 113B, and 113C illustrated in FIGS. 2, 6, 10, and 13.

The invention claimed is:

1. A drive assist system to be applied to a vehicle, the drive assist system comprising:
   an occupant monitoring apparatus configured to monitor a physical state of an occupant of the vehicle to acquire monitoring information of the occupant, wherein the occupant includes a driver of the vehicle;
   a determination apparatus configured to determine a traveling state and a stopped state of the vehicle; and
   a drive assist control apparatus including one or more processors, and one or more memories having instructions, when executed by the one or more processors, causing the one or more processors to be configured to:
   determine that sleep duration of the occupant is less than a predetermined time and quality of sleep of the occupant is lower than a predetermined level on a basis of the monitoring information acquired by the occupant monitoring apparatus; and
   in response to (1) determining that the sleep duration of the occupant is less than the predetermined time and the quality of sleep of the occupant is lower than the predetermined level and (2) determining, by the determination apparatus, that the vehicle is in the stopped state, execute a control to secure safe traveling of the vehicle by restricting a driving operation to be performed by the driver.

2. The drive assist system according to claim 1, wherein the one or more processors are configured to set the predetermined time from accumulated sleep duration of the driver inside the vehicle on the basis of the monitoring information.

3. The drive assist system according to claim 2, wherein in a case: where the vehicle is determined to be in the stopped state; where the sleep duration at least of the driver in the occupant of the vehicle is determined as being less than the predetermined time; and where the quality of sleep at least of the driver in the occupant of the vehicle is determined as being lower than the predetermined level, the one or more processors are configured to perform a control of restricting sudden acceleration of the vehicle accompanied by an abrupt state change within a certain time period.

4. The drive assist system according to claim 2, wherein in a case: where the vehicle is determined to be in the stopped state; where the sleep duration at least of the driver in the occupant of the vehicle is determined as being less than the predetermined time; and where the quality of sleep at least of the driver in the occupant of the vehicle is determined as being lower than the predetermined level, the one or more processors are configured to perform a control of restricting sudden turning, performed by the driver, accompanied by an abrupt state change within a certain time period.

5. The drive assist system according to claim 2, wherein in a case: where the vehicle is determined to be in the stopped state; where the sleep duration at least of the driver in the occupant of the vehicle is determined as being less than the predetermined time; and where the quality of sleep at least of the driver in the occupant of the vehicle is determined as being lower than the predetermined level, the one or more processors are configured to perform a control of restricting a shift operation, performed by the driver, that possibly causes an abrupt state change within a certain time period.

6. The drive assist system according to claim 1, further comprising an information acquisition apparatus configured to acquire biometric information including sleep information of the occupant inside and outside the vehicle,
   wherein the one or more processors are configured to:
     store the biometric information received from the information acquisition apparatus in the one or more memories; and
     determine whether the sleep duration of the occupant is the predetermined time or more and whether the quality of sleep of the occupant is the predetermined level or higher on a basis of the monitoring information and the biometric information.

7. The drive assist system according to claim 6, wherein the one or more processors are configured to set the predetermined time from accumulated sleep duration of each day measured for the driver, on a basis of one or both of the monitoring information and the biometric information acquired by the information acquisition apparatus.

8. The drive assist system according to claim 7, wherein in a case: where the vehicle is determined to be in the stopped state; where the sleep duration at least of the driver in the occupant of the vehicle is determined as being less than the predetermined time; and where the quality of sleep at least of the driver in the occupant of the vehicle is determined as being lower than the predetermined level, the one or more processors are configured to perform a control of restricting sudden acceleration of the vehicle accompanied by an abrupt state change within a certain time period.

9. The drive assist system according to claim 7, wherein in a case: where the vehicle is determined to be in the stopped state; where the sleep duration at least of the driver in the occupant of the vehicle is determined as being less than the predetermined time; and where the quality of sleep at least of the driver in the occupant of the vehicle is determined as being lower than the predetermined level, the one or more processors are configured to perform a control of restricting sudden turning, performed by the driver, accompanied by an abrupt state change within a certain time period.

10. The drive assist system according to claim 7, wherein in a case: where the vehicle is determined to be in the stopped state; where the sleep duration at least of the driver in the occupant of the vehicle is determined as being less than the predetermined time; and where the quality of sleep at least of the driver in the occupant of the vehicle is determined as being lower than the predetermined level, the one or more processors are configured to perform a control of restricting a shift operation, performed by the driver, that possibly causes an abrupt state change within a certain time period.

11. The drive assist system according to claim 6, wherein in a case: where the vehicle is determined to be in the stopped state; where the sleep duration at least of the driver in the occupant of the vehicle is determined as being less than the predetermined time; and where the quality of sleep at least of the driver in the occupant of the vehicle is determined as being lower than the predetermined level, the one or more processors are configured to perform a control of restricting sudden acceleration of the vehicle accompanied by an abrupt state change within a certain time period.

12. The drive assist system according to claim 6, wherein in a case: where the vehicle is determined to be in the stopped state; where the sleep duration at least of the driver in the occupant of the vehicle is determined as being less than the predetermined time; and where the quality of sleep at least of the driver in the occupant of the vehicle is determined as being lower than the predetermined level, the one or more processors are configured to perform a control of restricting sudden turning, performed by the driver, accompanied by an abrupt state change within a certain time period.

13. The drive assist system according to claim 6, wherein in a case: where the vehicle is determined to be in the stopped state; where the sleep duration at least of the driver in the occupant of the vehicle is determined as being less than the predetermined time; and where the quality of sleep at least of the driver in the occupant of the vehicle is determined as being lower than the predetermined level, the one or more processors are configured to perform a control of restricting a shift operation, performed by the driver, that possibly causes an abrupt state change within a certain time period.

14. The drive assist system according to claim 1, wherein in a case: where the vehicle is determined to be in the stopped state; where the sleep duration at least of the driver in the occupant of the vehicle is determined as being less than the predetermined time; and where the quality of sleep at least of the driver in the occupant of the vehicle is determined as being lower than the predetermined level, the one or more processors are configured to perform a control of restricting sudden acceleration of the vehicle accompanied by an abrupt state change within a certain time period.

15. The drive assist system according to claim 1, wherein in a case: where the vehicle is determined to be in the stopped state; where the sleep duration at least of the driver in the occupant of the vehicle is determined as being less than the predetermined time; and where the quality of sleep at least of the driver in the occupant of the vehicle is determined as being lower than the predetermined level, the one or more processors are configured to perform a control of restricting sudden turning, performed by the driver, accompanied by an abrupt state change within a certain time period.

16. The drive assist system according to claim 1, wherein in a case: where the vehicle is determined to be in the stopped state; where the sleep duration at least of the driver in the occupant of the vehicle is determined as being less than the predetermined time; and where the quality of sleep at least of the driver in the occupant of the vehicle is determined as being lower than the predetermined level, the one or more processors are configured to perform a control of restricting a shift operation, performed by the driver, that possibly causes an abrupt state change within a certain time period.

17. The drive assist system according to claim 1, wherein the driving operation to be restricted is (1) sudden acceleration of the vehicle accompanied by an abrupt state change within a certain time period, (2) sudden turning, performed by the driver, accompanied by an abrupt state change within a certain time period, or (3) a shift operation, performed by the driver, that possibly causes an abrupt state change within a certain time period.

18. The drive assist system according to claim 1, wherein the stopped state is a state where an ignition key is in an OFF position.

* * * * *